US009885731B2

(12) United States Patent
Huang et al.

(10) Patent No.: US 9,885,731 B2
(45) Date of Patent: Feb. 6, 2018

(54) MEDICAL TESTED OBJECT AUTO-EJECTION STRUCTURE AND BLOOD-GAS ANALYZER USING SAME

(71) Applicant: EDAN INSTRUMENTS, INC., Nanshan Shenzhen (CN)

(72) Inventors: Gaoxiang Huang, Shenzhen (CN); Zhixiang Zhao, Shenzhen (CN)

(73) Assignee: EDAN INSTRUMENTS, INC., Shenzhen (CN)

( * ) Notice: Subject to any disclaimer, the term of this patent is extended or adjusted under 35 U.S.C. 154(b) by 191 days.

(21) Appl. No.: 14/773,459

(22) PCT Filed: Mar. 12, 2013

(86) PCT No.: PCT/CN2013/072478
§ 371 (c)(1),
(2) Date: Sep. 8, 2015

(87) PCT Pub. No.: WO2014/134837
PCT Pub. Date: Sep. 12, 2014

(65) Prior Publication Data
US 2016/0018425 A1    Jan. 21, 2016

(30) Foreign Application Priority Data

Mar. 7, 2013    (CN) .......................... 2013 1 0073577

(51) Int. Cl.
*G01N 35/00*    (2006.01)
*B01L 9/00*    (2006.01)
(Continued)

(52) U.S. Cl.
CPC .......... *G01N 35/00584* (2013.01); *B01L 9/00* (2013.01); *B01L 9/50* (2013.01);
(Continued)

(58) Field of Classification Search
CPC ........... G01N 33/4875; G01N 33/4925; G01N 2035/00108; G01N 2035/00277;
(Continued)

(56) References Cited

U.S. PATENT DOCUMENTS

2006/0133956 A1*  6/2006  Hamanaka ................ B01L 9/52
                                                                  422/68.1
2008/0229808 A1*  9/2008  Lee ..................... G01N 33/4875
                                                                  73/61.41
(Continued)

FOREIGN PATENT DOCUMENTS

CN            1397013 A     2/2003
CN          102007409 A     4/2011
(Continued)

OTHER PUBLICATIONS

International Search Report dated Nov. 11, 2013.

*Primary Examiner* — Jennifer Wecker
(74) *Attorney, Agent, or Firm* — Symbus Law Group, LLC; Clifford D. Hyra

(57) ABSTRACT

A medical tested object auto-ejection structure comprises a detection instrument and a tested object (1). An insertion port is formed in the detection instrument. When the tested object (1) is inserted in the instrument through the insertion port, the bottom end of the tested object (1) presses a bulge (21) used for rebounding, and a raised step (11) arranged on the surface of one side of the tested object (1) is locked on a clamping buckle (31) arranged at a position corresponding to the step on the instrument simultaneously, and after a test is finished, the instrument releases the locking of the clamping buckle (31) for the tested object (1) by a transmission device, and the tested object (1) is ejected from the instrument in time under the action of the bulge (21) used for rebounding, thus solving the problem of forgetting to pull (Continued)

the tested object out or inability to pull it out in time, and improving the reliability of the product.

9 Claims, 8 Drawing Sheets

(51) Int. Cl.
*G01N 33/49* (2006.01)
*G01N 33/487* (2006.01)
*F16K 1/24* (2006.01)
*B01L 3/00* (2006.01)
*G01N 21/84* (2006.01)

(52) U.S. Cl.
CPC ............ *B01L 9/52* (2013.01); *G01N 33/4875* (2013.01); *G01N 33/4925* (2013.01); *B01L 2200/04* (2013.01); *B01L 2300/0825* (2013.01); *F01L 2105/00* (2013.01); *F16K 1/24* (2013.01); *G01N 21/8483* (2013.01); *G01N 35/00693* (2013.01); *G01N 35/00712* (2013.01); *G01N 2035/00108* (2013.01); *G01N 2035/00277* (2013.01); *Y10T 436/115831* (2015.01)

(58) Field of Classification Search
CPC ......... G01N 21/8483; G01N 35/00584; G01N 35/00693; G01N 35/00712; B01L 2200/04; B01L 2300/0825; B01L 9/00; B01L 9/50
See application file for complete search history.

(56) References Cited

U.S. PATENT DOCUMENTS

| | | | | |
|---|---|---|---|---|
| 2009/0227854 | A1* | 9/2009 | Ohama | A61B 5/1468 600/345 |
| 2010/0012530 | A1* | 1/2010 | Watanabe | A61B 5/14532 205/792 |
| 2012/0143085 | A1* | 6/2012 | Sauers | A61B 5/14532 600/573 |
| 2015/0260743 | A1* | 9/2015 | Huang | F16K 1/24 436/50 |

FOREIGN PATENT DOCUMENTS

| | | | | |
|---|---|---|---|---|
| CN | 102734529 | A * | 10/2012 | ............ F16K 1/24 |
| TW | M420307 | U1 | 1/2012 | |
| WO | 2008055199 | A1 | 5/2008 | |

* cited by examiner

MEDICAL TESTED OBJECT AUTO-EJECTION STRUCTURE AND BLOOD-GAS ANALYZER USING SAME

FIELD OF THE INVENTION

The invention relates to the field of a mechanical ejection structure of medical equipment, and specifically to a medical tested object auto-ejection structure.

BACKGROUND OF THE INVENTION

In the medical field, when a sample is tested, a tested object (for example, blood, a tested card used in blood gas analysis equipment) is inserted into a test instrument for testing and analysis. This form of testing is widely used in medical equipment. When the test is completed, the prompt that the tested object should be pulled out is very important. If the tested object is pulled out too early, the instrument may be damaged and hence the correct measurements cannot be obtained, if the tested object is pulled out late, the control for the tested object may be stopped as the instrument completes the test, causing the residue in the tested object to flow out and contaminate the instrument, etc. Currently, on the market, an electronic lighting display form is generally adopted as a prompt after the test is completed. For the electronic lighting prompt, after the test of the tested object is finished, the color of the electronic lights is changed to indicate the completion of the test. This requires that the staff shall operate according to the indication of the electronic lights after the test is finished. If the staff is not nearby, this will result in the risk that the tested object is not pulled out in time and hence causes the tested object to contaminate the instrument.

Therefore, the prior art has a defect.

SUMMARY OF THE INVENTION

The Technical Problem

To overcome the abovementioned defects, the invention aims at providing a medical tested object auto-ejection structure and a blood gas analyzer using the structure.

The Technical Solution

The object of the invention is obtained through the following technical solution:

A medical tested object auto-ejection structure in the invention includes a detection instrument and a tested object, an insertion port is formed in the detection instrument, the tested object is inserted in the instrument through the insertion port, a rebounding device pressing against the top of the tested object is disposed right under the tested object after the tested object is inserted, the rebounding device is disposed on a base of the detection instrument, a raised step is arranged on the surface of one side of the tested object, a clamping buckle device locking and releasing the step through a transmission device is arranged at a position corresponding to the upper surface of the raised step, on the detection instrument.

Furthermore, the tested object is a medical test card.

Furthermore, the rebounding device includes a bulge, the bulge passes through an opening port arranged on the upper surface of the base of the detection instrument, the step which cannot pass through the opening port is arranged at the bottom end of the bulge, a column body is arranged at the bottom of the step, a spring used for rebounding is sleeved on the column body, the bottom end of the column body is disposed on the base.

Still furthermore, a liquid-withdrawing needle used for inserting into the tested object to withdraw liquid is arranged on the upper surface of the base, under the state that the bulge is not pressed tightly and retracted by the tested object, the height of the bulge which passes through the upper surface of the base of the detection instrument is higher than the height of the liquid-withdrawing needle.

Still furthermore, the clamping buckle device includes a tension rod, a clamping buckle locking the raised step is arranged at the front end of the tension rod, the spring pressing against the detection instrument is disposed at the back end of the tension rod.

Still furthermore, the shape of the clamping buckle is a slope inclining from up to down.

Still furthermore, the transmission device includes a lever and a gear, one end of the lever presses against and is connected with the tail end of the tension rod, and the other end of the lever presses against a boss arranged on the gear.

Still furthermore, the surface of the boss which is arranged on the gear is a concave surface.

Still furthermore, the end which the lever and the boss press against and the boss are both slope-shaped structures which match with each other.

A blood gas analyzer in the invention includes a medical tested object auto-ejection structure.

Effective Results

According to the technical solution provided by the invention, an insertion port is formed in the detection instrument. When the tested object is inserted in the instrument through the insertion port, the bottom end of the tested object presses a bulge used for rebounding, and a raised step arranged on the surface of one side of the tested object is locked on a clamping buckle arranged at a position corresponding to the step on the instrument simultaneously. After a test is finished, the instrument releases the locking of the clamping buckle for the tested object by a transmission device, and the tested object is ejected from the instrument in time under the action of the bulge used for rebounding, thus solving the problem of forgetting to pull out the tested object or not being able to pull it out in time, and improving the reliability of the product.

BRIEF DESCRIPTION OF THE DRAWINGS

In order to be described easily, the invention is described with the following preferred examples and figures in details.

DETAILED DESCRIPTION OF THE EMBODIMENT

The invention will be further described in more details and the object, the technical solution and the advantages of the invention will be more apparent with the combination of the following drawings and embodiments. It shall be understood that the embodiments described herein are only used for explaining the invention but do not limit the invention.

Figure 1:
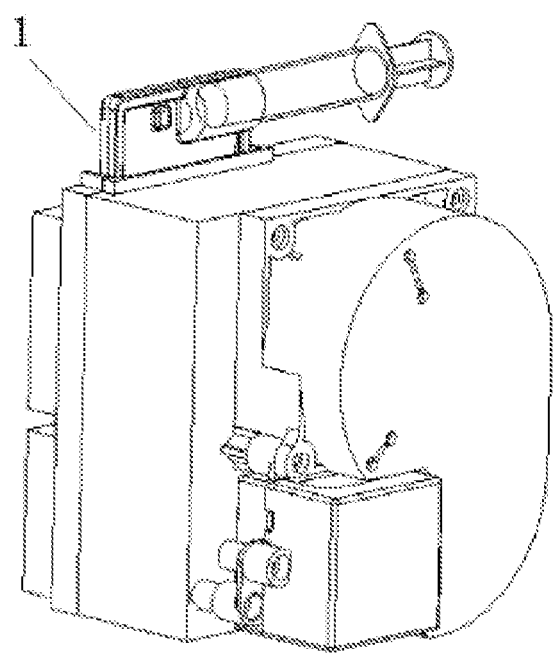
FIG. 1 is a whole assembly diagram of a medical tested object auto-ejection structure.
Figure 2:
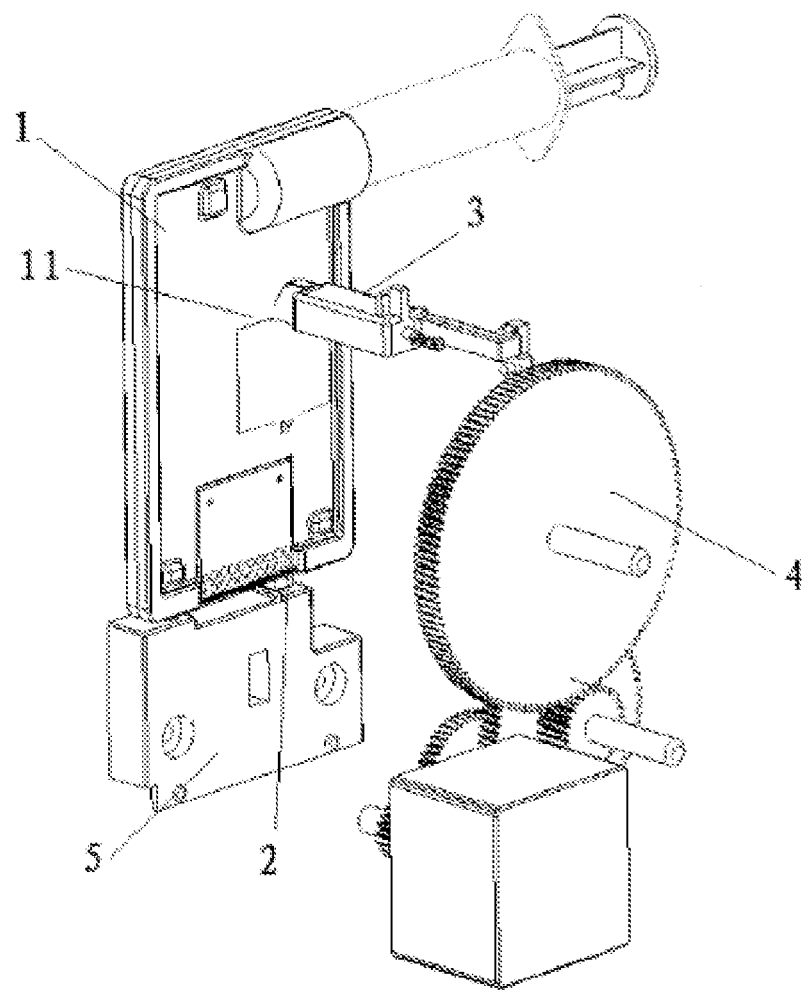
FIG. 2 is an exploded view of one example of a medical tested object auto-ejection structure.

As shown in FIGS. 1, 2, the invention has the following technical solution to solve the technical problems:

An insertion port is formed in the detection instrument, a tested object (for example, a technical solution of a test card, a test bottle or a test pipe which is loaded with a test liquid, preferably the test card, is described) is inserted into the instrument through the insertion port, a raised step 11 is arranged on the surface of one side of the test card 1, a rebounding device 2 and a clamping buckle device 3 arranged in the detection instrument are respectively assembled on a base 5 right under which the test card 1 is inserted, and the position corresponding to the front end of the raised step 11 arranged on the surface of one side of the test card 1, when the test card 1 is inserted into the insertion port arranged on the detection instrument, the test card 1 compresses the rebounding device 2 while a step 11 on the test card 1 is locked by the clamping buckle device 3 to fix the test card, the instrument starts to measure and analyze; when the measurement is completed, a transmission device of the instrument is operated so that the clamping buckle device 3 releases the step 11 on the test card 1, and the test card 1 is released, a test instrument is ejected under the action of the rebounding device 2 while the test card 1 is released, so that an auto-ejection structure is formed.

Figure 3:
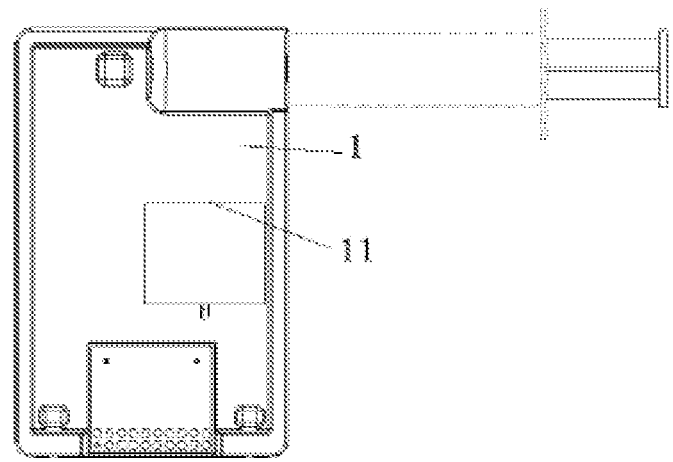
FIG. 3 is a diagram of a test card of a medical tested object auto-ejection structure.

The step 11 is arranged on the surface of any one side of the test card 1, so as to ensure that the test card 1 can be locked by the clamping buckle device 3 as is shown in FIG. 3.

Figure 5:
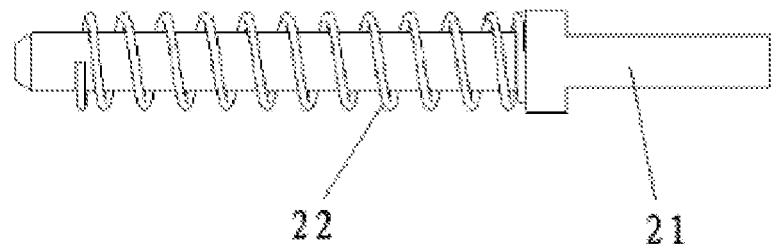
FIG. 5 is a diagram of a rebounding device of a medical tested object auto-ejection structure.
Figure 6:
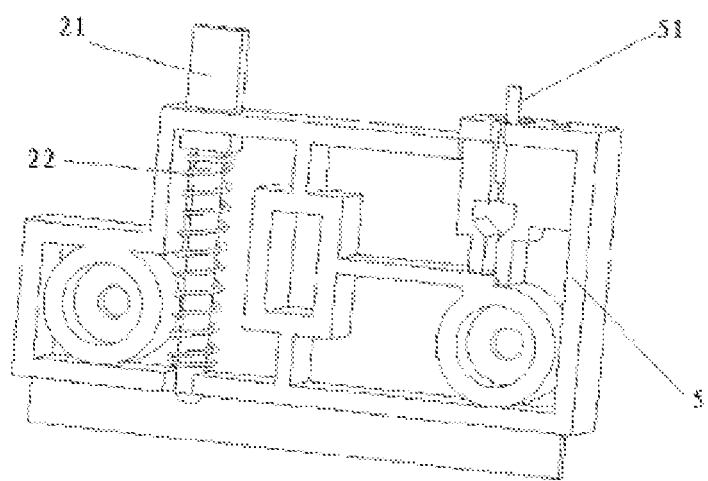
FIG. 6 is an assembly diagram of a rebounding device and a base of an instrument of a medical tested object auto-ejection structure.

As the preferable embodiment of the invention, as shown in FIGS. 2, 5, 6, the rebounding device 2 includes a bulge 21, the bulge 21 is provided with a step on the bottom end thereof and passes through an opening port arranged on the upper surface of a base 5. As the size of the step is larger than that of the opening port, the step cannot pass through the opening port. A column body through which a rebounding spring 22 is sleeved and passes is arranged under the step, the lower end of the column body is assembled at the lower end of the base 5 to form the rebounding device 2, one (or a plurality of) liquid-withdrawing steel needle 51 is assembled on the upper surface of the base 5 and projects from the upper surface of the base 5 simultaneously, and when the test card 1 is inserted, the steel needle 51 is inserted into the test card 1 to withdraw the test liquid in the test card 1. The whole rebounding device 2 is assembled under the insertion port of the test card 1 in the instrument, the bulge 21 is assembled on the base and projects from the upper surface of the base, and the projecting direction is preferable vertical to the upper surface and is in the same direction as the liquid-withdrawing needle 51. When the bulge 21 is not pressed tightly and retracted by the test card, the height of the bulge 21 preferably projecting from the upper surface of the base is higher than the height of the liquid-withdrawing steel needle 51, ensuring that the rebounding device 2 can be completely separated from the liquid-withdrawing steel needle 51 after the test is finished and when the rebounding device 2 rebounds the test card 1, and ensuring that the test card 1 is separated from the instrument. In addition, the rebounding device has many other ways which can be realized, for example, the shapes of the bulge and the opening port can be varied, the spring can be replaced with other spring pieces, the rebounding device can have a guiding groove, etc.

Figure 4:
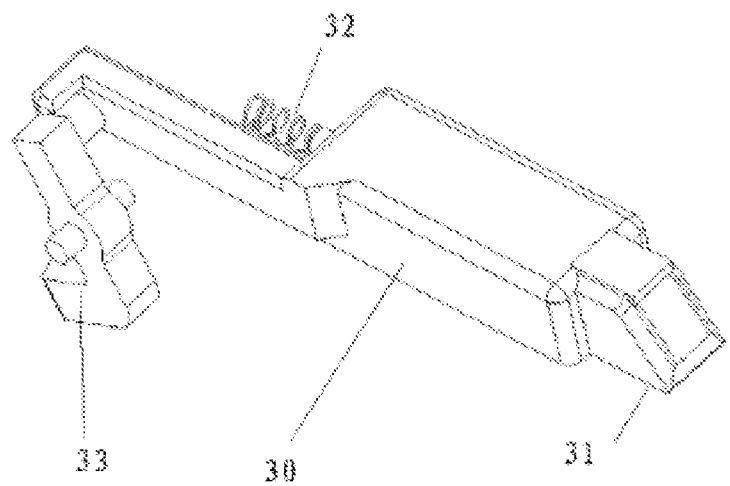
FIG. 4 is an assembly diagram of a clamping buckle and a transmission device of a medical tested object auto-ejection structure.

As shown in FIGS. 2, 4: the clamping buckle device 3 preferably includes, on the detection device, a tension rod 30 arranged at the position corresponding to the front end of the raised step arranged on the surface of one side of the inserted test card 1, a clamping buckle 31 is arranged at the front end of the tension rod 30 to clamp the front end of the raised step on the test card 1, the clamping buckle 31 is preferably a slope-shaped structure inclining from up to down, the slope-shaped structure ensures that the test card 1 can easily be inserted through the slope when it is inserted from above, the bottom end of the slope also can buckle the step 11 on the test card after the insertion, the spring 32 assembled on the back end of the tension rod 30 presses against the device and is used for ensuring that the clamping buckle 31 on the tension rod 30 can enable the clamping buckle device 3 to remain in the state of locking the test card 1 only by the spring force of the spring 32 in the case of no external force, and the detection instrument enables the clamping buckle device 3 to move forward and backward within the stroke of the spring through the transmission device, so as to lock and loosen the test card. Of course, the clamping buckle also can have other shapes, for example, rectangular, hook-shape, triangle, etc.

Figure 7:
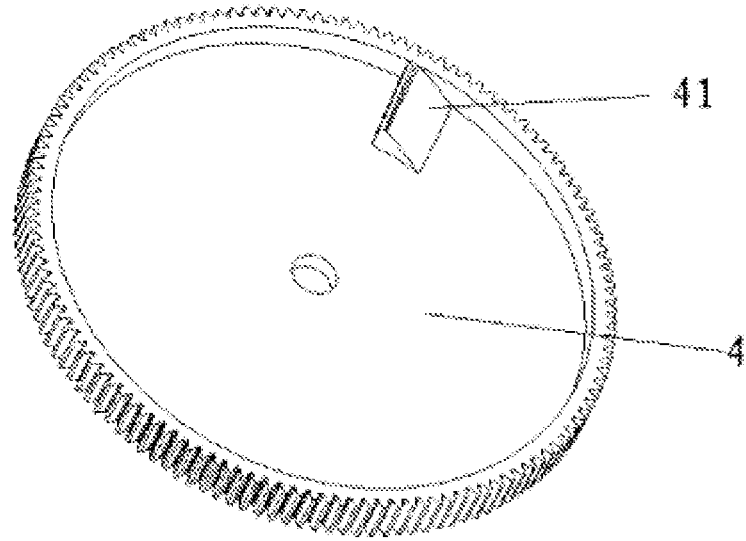
FIG. 7 is a diagram of a transmission gear of a medical tested object auto-ejection structure.

As shown in FIGS. 2, 4, 7, the transmission device preferably includes a lever pressing against and connecting the tail end of the tension rod 30, one head of the lever 33 is associated with a gear 4 and assembled in the instrument to form the transmission device, one boss 41 arranged at the position corresponding to the other head of the lever 33 on the gear 4 is used for controlling the movement of the lever 33, when the boss 41 does not press against the lever at the position where the gear rotates, as the clamping buckle device 3 loses external force, the state where the clamping buckle device 3 locks the test card 1 is maintained only under the action of the spring force of the spring 32 itself; when the boss 41 presses against one end of the lever 33 at the position where the gear rotates, the other head of the lever 33 connecting the tail end of the tension rod 30 is pulled up, and the clamping buckle 31 on the tension rod 30 is pulled apart, so that the clamping buckle device 3 is under the opening state. As the preferable solution of the invention, the lever 33 presses against the boss 41 on the gear to realize the control for the opening and locking of the step 11 on the test card 1, and the surface of the boss 41 which is arranged on the gear is a concave surface. The concave surface is mainly used for ensuring that the gear 4 can avoid the lever 33 not to provide external force for the clamping buckle device 3 when the instrument is under the normal state, thus ensuring that the clamping buckle device is always under the locking state, only when the boss 41 jacks up the lever 33, the boss 41 can pull up the clamping buckle device 3 to release the test card 1. As a gear linkage device driven by a motor has been provided in the instrument, the invention preferably selects the boss of the gear to provide control power for the clamping buckle device, likewise, the end which the lever 33 and the boss press against and the boss 41 both preferably adopt slope structures which match with each other, thus conveniently sliding and jacking up during the control process; certainly, the transmission device also can provide power to press against and release the lever 33 through the powering-on and powering-off of an electromagnetic valve controlled by software, etc. only by ensuring that the clamping buckle device can be provided with pulling force in time to release the test card after the test.

Figure 8:
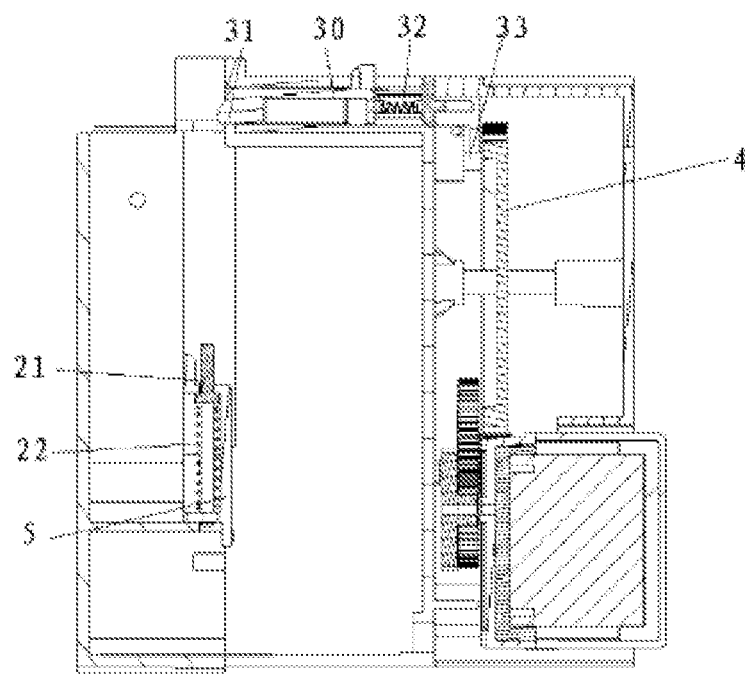
FIG. 8 is a cross-section diagram of an instrument when a medical tested object auto-ejection structure is not inserted into a test card.

When the test card 1 is not inserted, the gear 4 is under the initial state. At this time, the boss 41 on the gear 4 is far away from the lever 33 on the clamping buckle device 3, and the clamping buckle device 3 is under the locking state; the bulge 21 is ejected upward under the action of the spring 22 by the rebounding device 2, as shown in FIG. 8.

Figure 9:
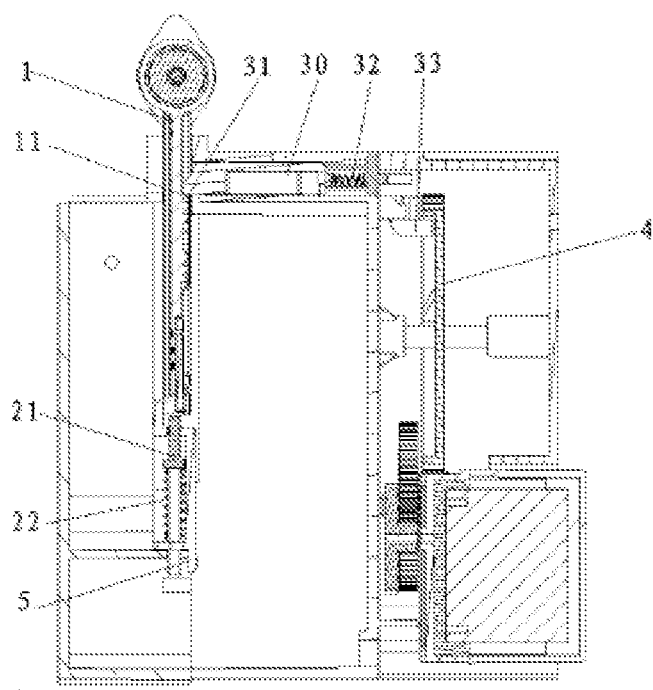
FIG. 9 is a cross-section diagram of an instrument when a medical tested object auto-ejection structure is inserted into a test card and under locking state.

When the test card 1 is inserted, the test card 1 presses the bulge 21 on the rebounding device 2 downward so that the rebounding spring 22 assembled on the rebounding device 2 is under a compacted state, meanwhile, the liquid-withdrawing steel needle 51 is inserted into the test card 1 to form a liquid-withdrawing passage, and the step 11 on the test card 1 slides to the lower side of the clamping buckle 31 on the clamping buckle device 3, so that the clamping buckle 31 locks the test card 1, as shown in FIG. 9.

Figure 10:
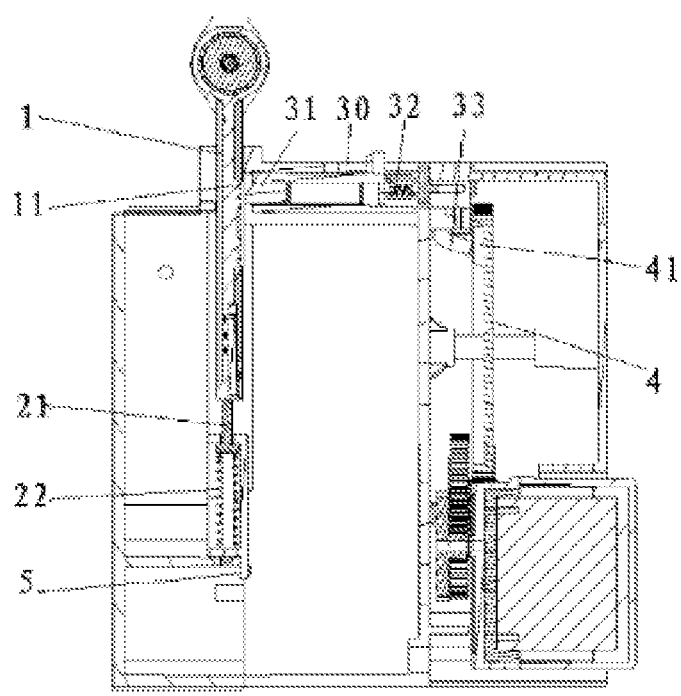
FIG. 10 is a cross-section diagram of an instrument when a medical tested object auto-ejection structure is inserted into a test card and ejection state.

After the test, the gear 4 in the instrument rotates, so that the boss 41 jacks up the lever 33 on the clamping buckle device 3, the tension rod 30 on the clamping buckle device 3 is pulled back, the clamping buckle 31 at the front end of the tension rod 30 releases the step 11 on the test card 1, and meanwhile, the boss 21, under the action of the force of the spring 22 of the rebounding device 2, accelerates upward and springs up the test card 1 from the rebounding device to be separated from the liquid-withdrawing steel needle 51 and from the instrument, finishing the test as is shown in FIG. 10.

The above-mentioned are only preferred embodiments of the invention and do not limit the invention, any modification, equal replacement and improvement made within the spirit and the principle of the invention shall be comprised in the protection scope of the invention.

The invention claimed is:

1. A medical tested object auto-ejection structure, comprising a detection instrument and a tested object, an insertion port formed in the detection instrument, the tested object is inserted in the instrument through the insertion port, wherein, a rebounding device pressing against the top of the tested object is arranged right under the tested object after the tested object is inserted, the rebounding device is disposed on a base of the detection instrument, a raised step is arranged on the surface of one side of the tested object, and a clamping buckle device locking and releasing the step through a transmission device is arranged at a position corresponding to the upper surface of the raised step, on the detection instrument, wherein the rebounding device comprises a bulge, and the bulge passes through an opening port arranged on an upper surface of the base of the detection instrument; and a liquid-withdrawing needle configured for being inserted into the tested object to withdraw liquid is arranged on the upper surface of the base, and wherein in a state where the bulge is not pressed tightly and is retracted by the tested object, the height of the bulge which passes through the upper surface of the base of the detection instrument is higher than the height of the liquid-withdrawing needle.

2. A medical tested object auto-ejection structure according to claim 1, wherein the tested object is a medical test card.

3. A medical tested object auto-ejection structure according to claim 1, wherein the step which cannot pass through the opening port is arranged at the bottom end of the bulge, a column body is arranged at the bottom of the step, a spring used for rebounding is sleeved on the column body, and the bottom end of the column body is disposed on the base.

4. A medical tested object auto-ejection structure according to claim 3, wherein the clamping buckle device comprises a tension rod and a clamping buckle element, the clamping buckle element locking the raised step is arranged at the front end of the tension rod, and the spring pressing against the detection instrument is disposed at the back end of the tension rod.

5. A medical tested object auto-ejection structure according to claim 4, wherein one surface of the clamping buckle element facing the raised step is a slope inclining from up to down.

6. A medical tested object auto-ejection structure according to claim 4, wherein the transmission device comprises a lever and a gear, one end of the lever presses against and is connected with the tail end of the tension rod, and the other end of the lever presses against a boss arranged on the gear.

7. A medical tested object auto-ejection structure according to claim 6, wherein the surface of the boss which is arranged on the gear is a concave surface.

8. A medical tested object auto-ejection structure according to claim 6, wherein the end which the lever and the boss press against and the boss are both slope-shaped structures which match with each other.

9. A blood gas analyzer, wherein the blood gas analyzer comprises a medical tested object auto-ejection structure of claim 1.

* * * * *